United States Patent
Fujino et al.

(10) Patent No.: US 12,111,307 B2
(45) Date of Patent: Oct. 8, 2024

(54) METHOD OF ASSESSING AGING OF ERYTHROCYTES

(71) Applicant: INSTITUTE OF RHEOLOGICAL FUNCTIONS OF FOOD, Fukuoka (JP)

(72) Inventors: Takehiko Fujino, Fukuoka (JP); Shiro Mawatari, Fukuoka (JP); Tsunemichi Kawa, Kanagawa (JP); Tetsuji Koyama, Kanagawa (JP); Toyoharu Yamashita, Fukuoka (JP)

(73) Assignee: INSTITUTE OF RHEOLOGICAL FUNCTIONS OF FOOD, Fukuoka (JP)

( * ) Notice: Subject to any disclaimer, the term of this patent is extended or adjusted under 35 U.S.C. 154(b) by 974 days.

(21) Appl. No.: 16/973,172

(22) PCT Filed: Jun. 10, 2019

(86) PCT No.: PCT/JP2019/022873
§ 371 (c)(1),
(2) Date: Dec. 8, 2020

(87) PCT Pub. No.: WO2019/240061
PCT Pub. Date: Dec. 19, 2019

(65) Prior Publication Data
US 2021/0255165 A1  Aug. 19, 2021

(30) Foreign Application Priority Data
Jun. 15, 2018  (JP) .................. 2018-115021

(51) Int. Cl.
*G01N 15/10* (2024.01)
*G01N 15/01* (2024.01)
*G01N 33/49* (2006.01)

(52) U.S. Cl.
CPC ........... *G01N 33/491* (2013.01); *G01N 15/10* (2013.01); *G01N 2015/012* (2024.01);
(Continued)

(58) Field of Classification Search
CPC ................. G01N 33/491; G01N 15/10; G01N 2015/1028; G01N 2015/012; G01N 2015/1006; G01N 2800/7042
See application file for complete search history.

(56) References Cited

U.S. PATENT DOCUMENTS
2009/0285892 A1  11/2009  Sakthivel et al.

FOREIGN PATENT DOCUMENTS
JP  H7-51521   2/1995
JP  2005-164296  6/2005
(Continued)

OTHER PUBLICATIONS

Bransky, A., et al., "Correlation between erythrocytes deformability and size: A study using a microhannel based cell analyzer", Microvascular Research, 73, pp. 7-13. (Year: 2007).*
(Continued)

*Primary Examiner* — Benjamin L Lebron
(74) *Attorney, Agent, or Firm* — GREENBLUM & BERNSTEIN, P.L.C.

(57) ABSTRACT

A method for assessing aging of erythrocytes that includes preparing an erythrocyte suspension from a blood sample; allowing the erythrocyte suspension to pass through a first filter, separating aged erythrocytes that do not pass through the first filter, and non-aged erythrocytes that pass through the first filter, and to calculate a deformability of erythrocytes, allowing the separated non-aged erythrocyte suspension to pass through a second filter having micropores which diameter is smaller than the first filter, separating mild aged erythrocytes that do not pass through the second filter and
(Continued)

juvenile erythrocytes that pass through the second filter, and to calculate a deformability of the non-aged erythrocytes; and assessing aging of erythrocytes, using the deformability of erythrocyte and the deformability of non-aged erythrocyte.

2 Claims, 4 Drawing Sheets

(52) U.S. Cl.
CPC ............ *G01N 2015/1006* (2013.01); *G01N 2015/1028* (2024.01); *G01N 2800/7042* (2013.01)

(56) References Cited

FOREIGN PATENT DOCUMENTS

| | | | | |
|---|---|---|---|---|
| JP | 2005-241378 | | 9/2005 | |
| WO | WO-2013067415 A1 | * | 5/2013 | ............ A61P 25/00 |

OTHER PUBLICATIONS

Canham, P., "Difference in geometry of young and old human erythrocytes explained by a filtering mechanism", Circulation Research, 25, pp. 39-45, Jul. 1969.*

Sousa et al., "A review of hemorheology: Measuring techniques and recent advances", Korea-Australia Rheology Journal, 2016, 28(1):1-22.

Odashiro et al., "Impaired deformability of circulating erythrocytes obtained from nondiabetic hypertensive patients: investigation by a nickel mesh filtration technique", Clinical Hypertension, 2015, 21(17): 1-8.

Uesaka, "Red blood cell deformation performance using a new microporous filter (nickel mesh)", Journal of Japanese Society of Biorheology, 1991, 5(4):23-32 (w/ partial translation).

Ejima et al., "Relationship of high-density lipoprotein cholesterol and red blood cell filterability: cross-sectional study of healthy subjects", Clinical Hemorheology and Microcirculation, 2000, 22:1-7.

Maruyama et al., "A New Quantitative Investigation of Erythrocyte Filterability Based on Nickel Mesh Filtration Technique", Fukuoka Acta Medica, 2004, 96(6):131-138 (w/ partial translation).

Katsunuma et al., "Erythrocyte Membrane Fatty Acid, Fluidity and Deformability and their Significance to Atherosclerosis—Causal relationships with pathogenesis and progression of atherosclerosis-", The Journal of Japan Atherosclerosis Society, 1987, 15(1):43-54 (English summary on p. 54).

ISR for PCT/IP2019/022873, dated Sep. 3, 2019.

Extended European Search Report issued in corresponding European Patent Application No. 19819235.3, dated Jun. 28, 2021.

Bosch et al., "Determinants of Red Blood Cell Deformability in Relation to Cell Age," *Eur J. Haematol.*, Jan. 1, 1994, 52, pp. 35-41.

Nash et al., "Red Cell and Ghost Viscoelasticity. Effects of Hemoglobin Concentration and In Vivo Aging," *Biophysical Journal*, Jul. 1, 1983, 43, pp. 63-73.

Youn et al., "Cell Deformability Monitoring Chips Based on Orifice-Length-Dependent Digital Lysis Rates," MEMS, Jan. 22-26, 2006, pp. 16-19.

* cited by examiner

[Fig. 1]
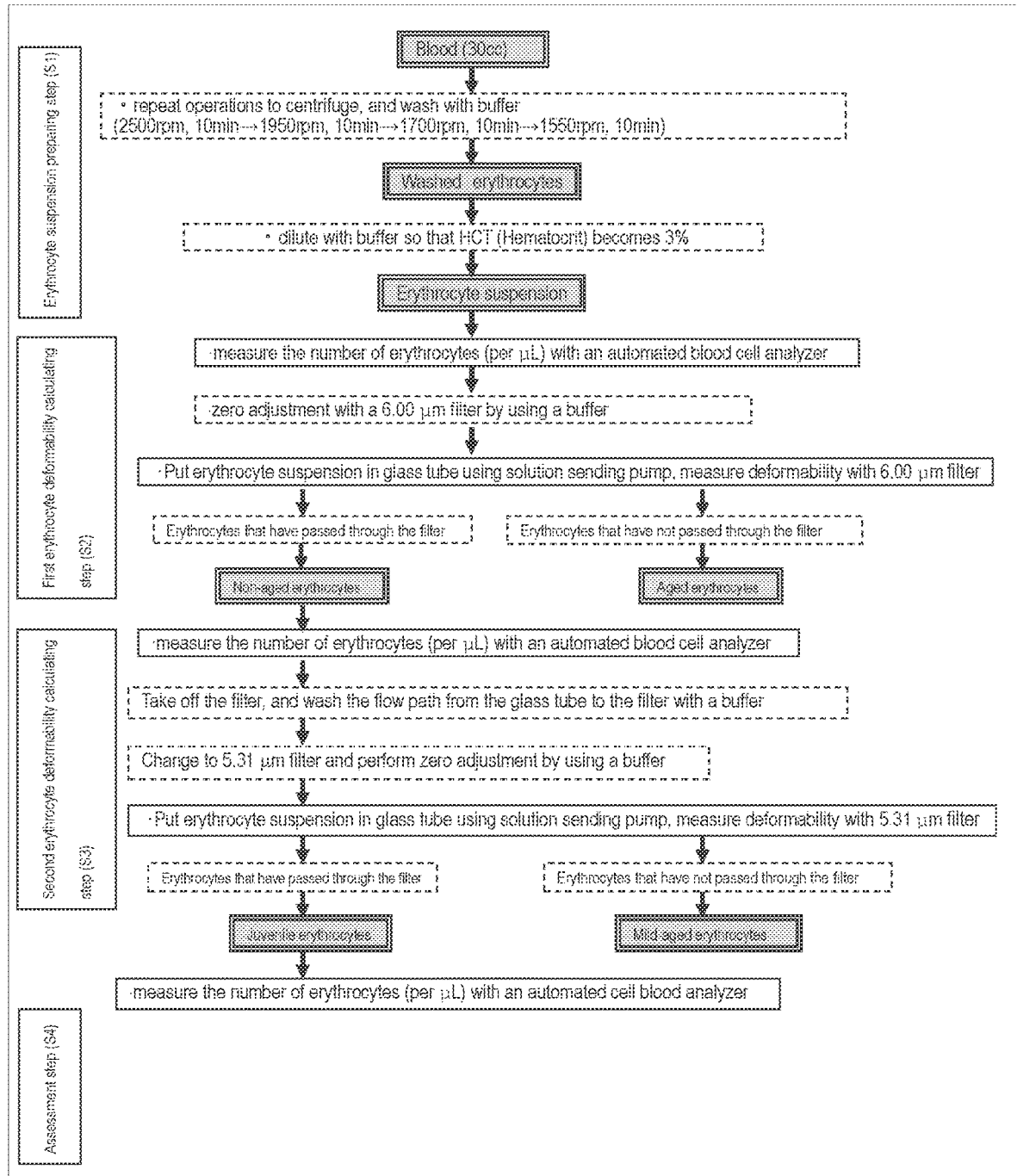

[Fig. 2]
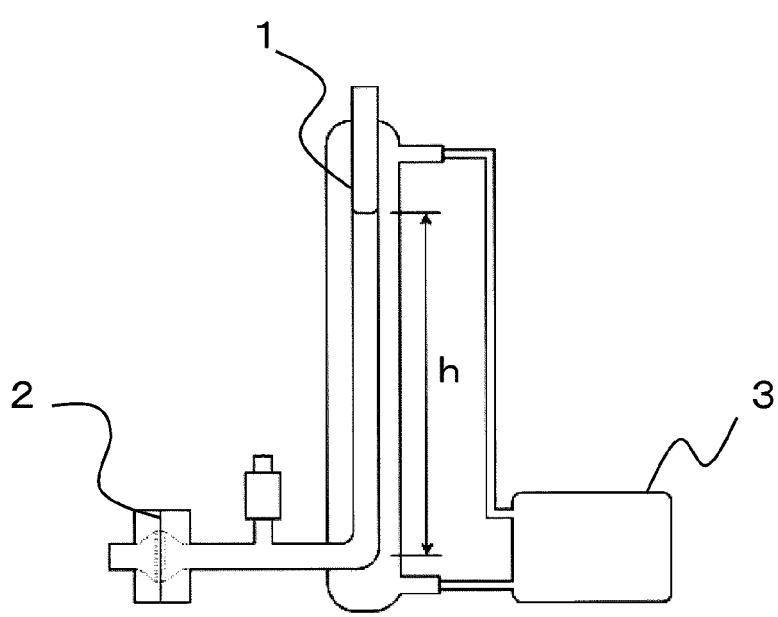
[Fig. 3]
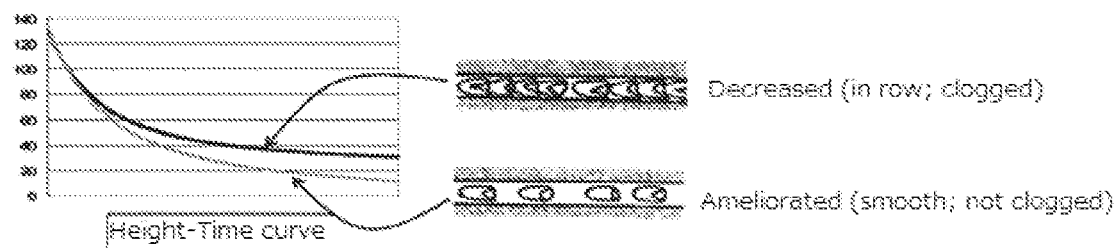

[Fig. 4]
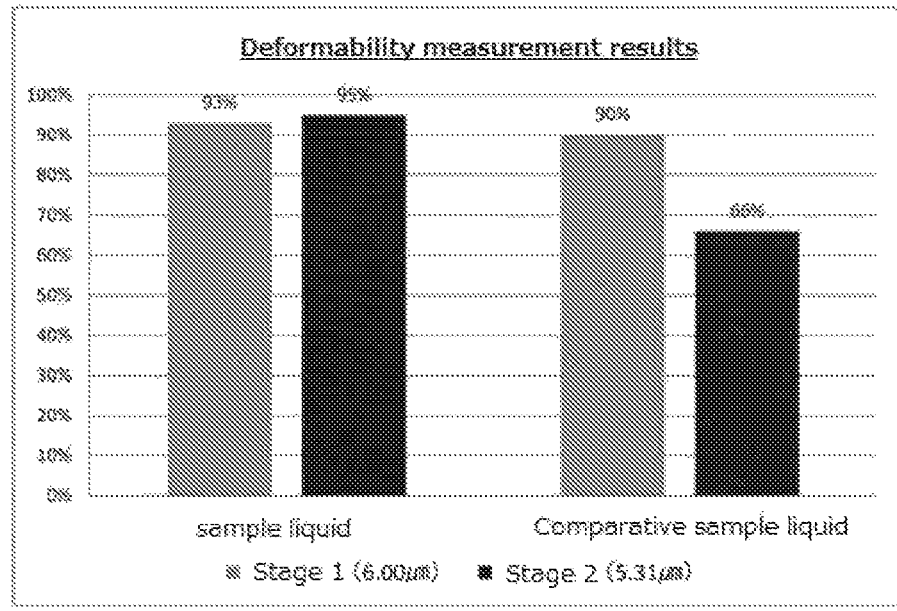
[Fig. 5]
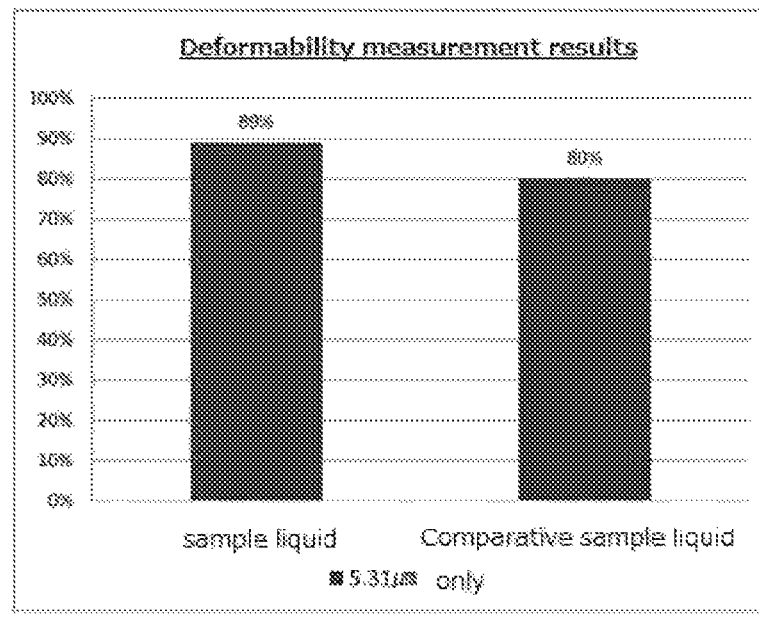

[Fig. 6]
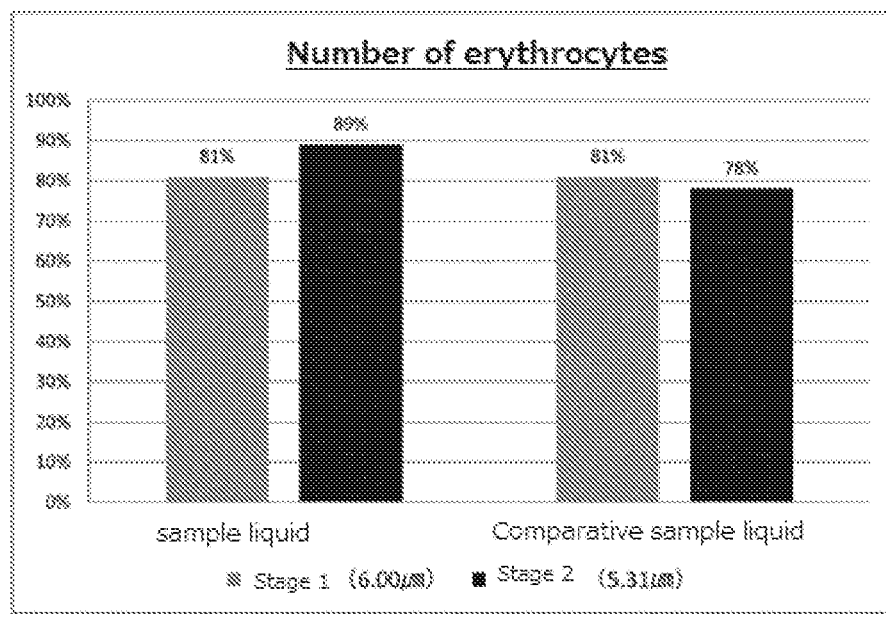
[Fig. 7]
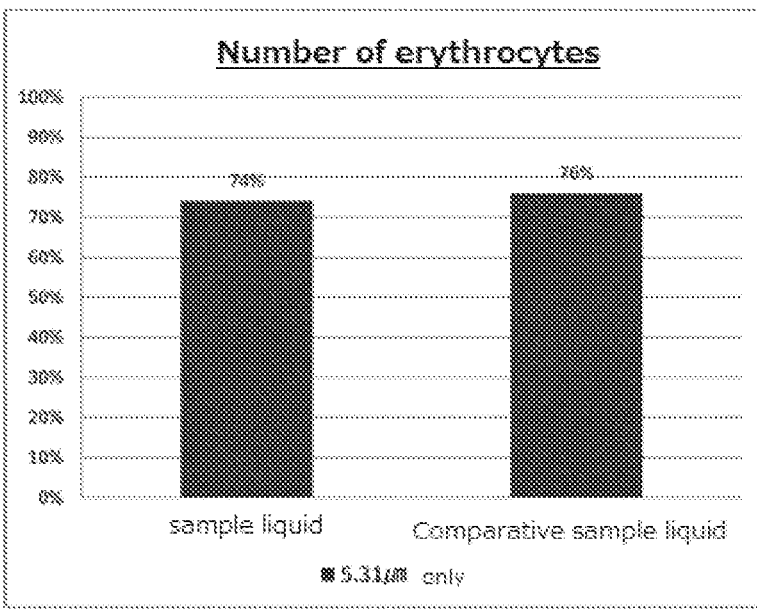

METHOD OF ASSESSING AGING OF ERYTHROCYTES

TECHNICAL FIELD

The present invention relates to a method for assessing aging of erythrocytes in blood, which is the cause of ghosting of capillary blood vessels.

BACKGROUND ART

By using microscopes for capillary blood vessel that are recently attracting press attention, it is possible to observe capillary blood vessels that cannot normally be seen, and it is possible to find ghosting of capillary blood vessels, such as disappearing, shortening or reducing in number of capillary blood vessels. This ghosting of capillary blood vessels can occur throughout the body, and there is a risk of inducing not only influence on skin state, which is visible, such as wrinkles or sagging of skin, but also severe diseases such as osteoporosis, dementia, and lifestyle-associated diseases (diabetes, hypercholesteremia, etc.)

What is important during the process in which the flow of capillary blood vessels worsen and ghosts, is erythrocytes. This is because there is no function of constriction or expansion in the capillary blood vessels which contain no smooth muscle, and the erythrocytes pass through capillary blood vessels (about 5 μm) that are narrower than its own diameter (about 8 μm) by changing their shape to circulate throughout the body. The number of erythrocytes per μL of blood is 4 to 5 millions, and the volume of erythrocytes reaches 40 to 50% of the volume of blood. The lifetime of these erythrocytes is as short as about 120 days, and there exist erythrocytes at various stages ranging from juvenile erythrocytes to aged erythrocytes. Those associated with ghosting of capillary blood vessels the most are the aged erythrocytes of which deformability has decreased. The aged erythrocytes are clogged in the capillary blood vessels, and it becomes impossible to deliver substances necessary for life of the cells that form the capillary blood vessels ahead, and the ghosting is thus thought to progress.

Recently, methods or apparatuses for assessing such deformability of erythrocytes in blood are proposed. Apparatuses that have been developed in Japan include, for example, MCFAN HR 300 (Micro Channel Array Flow Analyzer, Japan, manufactured by MC health care). MCFAN is an apparatus of allowing collected blood to flow through something like a capillary blood vessel that has been artificially made with silicon, to observe the image. At first upon development, it has been admired as contributing a lot to the research of the deformability of erythrocytes. However, it has been then found that the credibility is low, and now it is only employed in a very limited number of hospitals.

Further, apparatuses that have been developed abroad include LORCA (Laser-assisted Optical Rotational Cell Analyzer, Netherlands, manufactured by Mechatronics) which deforms erythrocytes to an ellipse by imparting centrifugal stress by rotatable flow and assesses with the diffracted image of laser beam, and RheoScan-D (Korea, manufactured by RheoMeditech) which deforms erythrocytes to an ellipse by imparting shear stress with negative pressure, and assesses with an diffracted image of laser beam (non-patent document 1). RheoScan-D has characteristics that automatical measurement can be performed with whole blood, it is not necessary to clean after usage owing to disposable plastic microchips in the flow path, and the aggregation of erythrocytes can be also measured, etc.

However, the physiologic deformation of erythrocytes in vivo is a bended deformation, and attention should be paid to the fact that whether to measure the deformability by deforming the erythrocytes in an ellipse reflects the conditions of physiological microcirculation. Further, since the stress necessary for deformation in an ellipse is much larger than the stress necessary for bended deformation, there is a problem that particularly the measurement sensitivity is low with a low shear stress as compared to a method for measuring bended deformation.

PRIOR ART DOCUMENTS

Non-Patent Documents

[Non-patent document 1] Patricia C. Sousa, Fernando T. Pinho, Man uel A. Alves and Monica S. N. Oliveira, A review of hemorheology: Measuring techniques and recent advances, *Korea-Australia Rheology J*, 28(1), 1-22 (2016)

SUMMARY OF THE INVENTION

Object being Solved by the Invention

Conventional assessment methods assess aging of erythrocytes by using a deformability obtained with erythrocytes as a whole at various stages in the lifetime of about 120 days, and no apparatus that can obtain deformability of only aged erythrocytes, or erythrocytes excluding aged erythrocytes, or automated apparatus for this has been developed.

The ratio of aged erythrocytes, which is the cause of ghosting of capillary blood vessels, varies depending on each patient. If such assessment method or apparatus is developed, it would be possible to appropriately diagnose each patient for the development risks of complications such as diabetic retinopathy, nephropathy, etc., and it is estimated that clinical meaning is important.

The object of the present invention is to provide a method for assessing aging of erythrocytes that can assess aging of erythrocytes with higher accuracy and properly.

Means to Solve the Object

The present inventors focused on the rheology function such as flexibility or ability of flowing of erythrocytes in blood, which is very important for the prevention and treatment of lifestyle-associated diseases, and developed an apparatus for measuring deformability of erythrocytes using gravity nickel mesh filtration system, to provide erythrocyte deformability test.

By using this gravity nickel mesh filtration system (diameter of micropores of the filter: 3.2 μm), according to the results of an investigation by limiting to mild case of hyperlipidemia (total cholesterol level 260 mg/dl or less) for 139 subjects who had a medical check-up, the erythrocyte deformability showed a negative correlation between levels of neutral fat, and a positive correlation between HDL cholesterol levels (Ejima J, Ijichi T, Ohnishi Y, Maruyama T, Kaji Y, Kanaya S, Fujino T, Uyesaka N and Ohmura T: Relationship of high-density lipoprotein cholesterol and erythrocyte filterability: cross-sectional study of healthy subjects. *Clin Hemorheol Microcirc* 22: 1-7, 2000.).

Further, for 101 patients having hypertension, an investigation using a filter (diameter of micropores: 4.94 μm) has revealed that the erythrocyte deformability showed a negative correlation between average blood pressure (K. Odashiro et al, Impaired deformability of circulating erythrocytes obtained from nondiabetic hypertensive patients: investigation by a nickel mesh filtration technique, Clin Hypertens. 21:17, eCollection (2015)).

The present inventors have further made keen studies to assess aging of erythrocytes in blood with higher accuracy and properly, and as a result, by separating erythrocytes plural times to obtain deformability of erythrocytes in each of separating step, assessed aging of erythrocytes by using these levels, they found out to be possible to assess aging of erythrocytes with higher accuracy and properly, and thus ghosting of capillary blood vessels. The present invention has been thus completed.

Specifically, the present invention is as follows.

[1] A method for assessing aging of erythrocytes by using at least two types of filters having a plurality of micropores, the method comprising
an erythrocyte suspension-preparing step of preparing an erythrocyte suspension from a blood sample;
a first erythrocyte deformability calculating step of allowing the erythrocyte suspension to pass through a first filter, separating aged erythrocytes that do not pass through the first filter, and non-aged erythrocytes that pass through the first filter, and to calculate a deformability of erythrocytes contained in the erythrocyte suspension;
a second erythrocyte deformability calculating step of allowing the separated non-aged erythrocyte suspension to pass through a second filter having micropores of which diameter is smaller than the first filter, separating mild aged erythrocytes that do not pass through the second filter and juvenile erythrocytes that pass through the second filter, and to calculate a deformability of the non-aged erythrocytes contained in the non-aged erythrocyte suspension; and
an assessment step of assessing aging of erythrocytes by using the deformability of erythrocytes calculated in the first erythrocyte deformability calculating step, and the deformability of non-aged erythrocytes calculated in the second erythrocyte deformability calculating step.

[2]. The method for assessing aging of erythrocytes according to [1], wherein a passing ratio of erythrocytes is further calculated in the first erythrocyte deformability calculating step and/or the second erythrocyte deformability calculating step, to use the passing ratio for the assessment in the assessment step.

[3]. The method for assessing aging of erythrocytes according to [1] or [2], wherein a diameter of micropores of the first filter is 5.50 to 8.00 μm.

[4]. The method for assessing aging of erythrocytes according to any one of [1] to [3], wherein a diameter of micropores of the second filter is 3.00 to 6.00 μm.

Effect of the present invention

According to the method for assessing aging of erythrocytes of the present invention, aging of erythrocytes can be assessed with higher accuracy and properly. Therefore, the possibility of ghosting of capillary blood vessels can be accurately detected, and can be applied to diagnosis of various diseases.

BRIEF EXPLANATION OF DRAWINGS

FIG. 1
It is a diagram showing the method for assessing aging of erythrocytes of one embodiment of the present invention.
FIG. 2
It is a brief figure explaining the apparatus used in the method for assessing aging of erythrocytes of one embodiment of the present invention.
FIG. 3
It is a figure showing "height-time curve" obtained by the measurement results of the apparatus shown in FIG. 2.
FIG. 4
It is a graph showing the deformability of erythrocytes passing through the filter when using the multistage method (Example 1) of the present invention.
FIG. 5
It is a graph showing the deformability of erythrocytes passing through the filter when using the conventional single stage method.
FIG. 6
It is a graph showing the number of erythrocytes (ratio) that have passed through the filter when using the multistage method (Example 1) of the present invention.
FIG. 7
It is a graph showing the number of erythrocytes (ratio) that have passed through the filter when using the conventional single stage method.

MODE OF PRACTICING THE INVENTION

The assessing method for aging of erythrocytes of the present invention is a method for assessing aging of erythrocytes by using at least two types of filters having a plurality of uniform micropores, the method comprising
an erythrocyte suspension-preparing step of preparing an erythrocyte suspension from a blood sample;
a first erythrocyte deformability calculating step of allowing the erythrocyte suspension to pass through a first filter, separating aged erythrocytes that do not pass through the first filter, and non-aged erythrocytes that pass through the first filter, and to calculate a deformability of erythrocytes contained in the erythrocyte suspension;
a second erythrocyte deformability calculating step of allowing the separated non-aged erythrocyte suspension to pass through a second filter having micropores of which diameter is smaller than the first filter, separating mild aged erythrocytes that do not pass through the second filter and juvenile erythrocytes that pass through the second filter, and to calculate a deformability of the non-aged erythrocytes contained in the non-aged erythrocyte suspension; and
an assessment step of assessing aging of erythrocytes by using the deformability of erythrocytes calculated in the first erythrocyte deformability calculating step, and the deformability of non-aged erythrocytes calculated in the second erythrocyte deformability calculating step.

The method for assessing aging of erythrocytes of the present invention can assess aging of erythrocytes by using the apparatus for measuring deformability of erythrocytes described in "Toru Maruyama, Kazuhiko Okamoto, Quantitative analysis of deformability of erythrocytes by nickel mesh filtration system, Fukuoka Acta *Medica,* 95(6), 131-138(2004)".

In the method for assessing aging of erythrocytes of the present invention, in the first erythrocyte deformability calculating step and/or second erythrocyte deformability calculating step, it is preferred to calculate the passing ratio of erythrocytes, and to use this passing ratio in the assessment of the assessing step. Thereby, it is possible to make a more precise assessment of aging of erythrocytes.

Further, the method of the present invention can comprise further erythrocyte deformability calculating steps, such as a third erythrocyte deformability calculating step using a third filter, a fourth erythrocyte deformability calculating step using a fourth filter, etc., and to use the deformability or passing ratio of erythrocytes calculated in these steps for the assessment.

In the following, the method for assessing aging of erythrocytes of the present invention is explained in detail.

As shown in FIG. 1, the method for assessing aging of erythrocytes of one embodiment of the present invention comprises sequentially an erythrocyte suspension-preparing step (S1), a first erythrocyte deformability calculating step (S2), a second erythrocyte deformability calculating step (S3), and an assessment step (S4).

<Erythrocyte Suspension-Preparing Step>

The erythrocyte suspension-preparing step (S1) is a step of preparing erythrocyte suspension from a blood sample, and for example is a step of preparing an erythrocyte suspension by washing a blood sample collected from a test subject. Specifically, for example, a treatment of washing the collected blood by centrifugation with a buffer is repeated plural times, and then is diluted with a buffer so that the hematocrit (HCT) has a certain concentration, to prepare an erythrocyte suspension.

<First Erythrocyte Deformability Calculating Step>

The first erythrocyte deformability calculating step (S2) is a step of passing the erythrocyte suspension prepared in the erythrocyte suspension-preparing step (S1) through a first filter, to separate aged erythrocytes that do not pass through the first filter and non-aged erythrocytes that pass through the first filter, and to calculate a deformability of erythrocytes contained in the erythrocyte suspension.

As for the first filter used in the present invention, to ensure high quantitativeness and reproducibility, uniform filters of which shape, number and distribution of micropores are similar are preferred. Examples include nickel mesh filter manufactured by combining a photoresist method and special plating method. The first filter is preferred to have a structure that hardly confer mechanical stimulation to leukocytes which are mixed during preparation of erythrocyte suspension.

The diameter of micropores of the first filter can be appropriately changed according to the situation of the test subjects, while generally, it is preferably 5.50 to 8.00 µm, more preferably 5.60 to 7.00 µm, and further preferably 5.70 to 6.50 µm.

In this step, the deformability of erythrocytes is calculated. The deformability is an index showing the ability of the erythrocytes (non-aged erythrocytes) contained in the erythrocyte suspension to pass through the first filter. Various levels calculated by so-called filtration method such as difference of pressure when the erythrocyte suspension passes through the micropores of the filter, the passing time that a certain amount of erythrocyte suspension passes through, the flow rate (Q) of erythrocytes, etc. can be used.

Specifically, the method for calculating the deformability of the present invention can be calculated for example by using an apparatus as shown in FIG. 2. As it is shown in FIG. 2, to the vertical glass tube 1, a nickel mesh filter 2 (for example, diameter of micropores: 6.0 µm) is mounted via a Tygon tube, and the erythrocyte suspension is filtered from a certain height (for example 15 cm). By continuously measuring the pressure at that time, the height (h in FIG. 2)—time curve is obtained (see FIG. 3). By comparing with the height-time curve of a buffer not containing erythrocytes similarly obtained, and comparing the time at the time point where it has been decreased to a certain height (for example 10 cm), the deformability is quantified.

In the present step, further, the passing ratio of erythrocytes, specifically the ratio of aged erythrocytes that do not pass through the first filter, and the non-aged erythrocytes that pass through the filter is preferably calculated. By using this passing ratio in the assessment step, a more precise assessment can be made. The calculation of the passing ratio can be obtained by using a well-known blood cell analyzer, etc., by measuring at least two of the total number of erythrocytes contained in the erythrocyte suspension, the number of aged erythrocytes, and the number of non-aged erythrocytes.

<Second Erythrocyte Deformability Calculating Step>

The second erythrocyte deformability calculating step (S3) is a step of allowing the non-aged erythrocyte suspension that has been separated in the above-mentioned first erythrocyte deformability calculating step (S2) to pass through a second filter having micropores of which diameter is smaller than the first filter, to separate the mild aged erythrocytes that do not pass through the second filter and the juvenile erythrocytes that pass through the filter, and to calculate a deformability of the non-aged erythrocytes contained in the non-aged erythrocyte suspension.

As the non-aged erythrocyte suspension used in this step, the suspension separated in the first erythrocyte deformability calculating step (S2) can be directly used, or can be diluted with a buffer so that the hematocrit (HCT) has a certain concentration, and used.

The treatment of the present step is basically similar to the treatment of the first erythrocyte deformability calculating step (S2), while the filter to be used is different. Specifically, in the present step, a second filter having micropores of which diameter is smaller than that of the micropores of the first filter is used. The diameter of micropores of the second filter can be appropriately changed according to the results of the first erythrocyte deformability calculating step (S2), etc., while generally, it is preferably 3.00 to 6.00 µm, more preferably 3.50 to 5.80 µm, further preferably 4.00 to 5.50 µm, and particularly preferably 4.50 to 5.50 µm. Further, it is preferable that the difference with the diameter of micropores of the first filter is 0.1 to 2.0 µm, more preferably 0.3 to 1.5 µm, and further preferably 0.5 to 1.0 µm.

<Assessment Step>

The assessment step (S4) is a step of assessing the aging of erythrocytes using the deformability of erythrocytes calculated in the first erythrocyte deformability calculating step, and the deformability of non-aged erythrocytes calculated in the second erythrocyte deformability calculating step. In this step, additionally to the deformability of the erythrocytes and non-aged erythrocytes, it is preferred to use the passing ratio of the erythrocytes calculated in the first erythrocyte deformability calculating step and/or the second erythrocyte deformability calculating step. As such, a more precise assessment can be made.

Specifically, in this step, when the deformability is low, it is assessed that the erythrocytes are aged, and further by adding the assessment based on the passing ratio (the lower the passing ratio is, the more aged the erythrocytes are) at the same time or additionally, the aging of erythrocytes is assessed. As such, the possibility of ghosting of capillary blood vessels can be accurately detected, and can be applied to the diagnosis of the skin state such as wrinkles or sagging of skin, or diagnosis of osteoporosis, dementia, and lifestyle-associated diseases (diabetes, hypercholesteremia, etc.). Thus, early detection of diseases is possible.

Particularly, since the method for assessing aging of erythrocytes of the present invention assesses by using the deformability (and passing rate) in at least two or more separation steps, an assessment of aging of erythrocytes that is more precise than a conventional method can be made. Further, by changing the combination of the size of micropores of the filters according to the situation of the test subjects (age, blood pressure, diseases suffering from, chronic disease, etc.), a more adequate assessment can be made.

EXAMPLE

In the following, the present invention is explained in detail by referring to the Example. However, the present invention is not limited to the Example. The summary of the basic operations of the Example is shown in FIG. 1.

[Basic Operations]
(Erythrocytes Suspension-Preparing Step)

First, 30 cc of blood collected from a test subject is centrifuged at a rotation of 2500 rpm, for 10 minutes by using a centrifuge, and washed with a buffer. Then, by changing sequentially the rotation to 1950 rpm, 1700 rpm, 1550 rpm, centrifugation (10 minutes each) and washing with buffer are repeated to obtain washed erythrocytes. The obtained washed erythrocytes are diluted with a buffer, to prepare an erythrocyte suspension with a hematocrit (HCT) of 3%. The number of erythrocytes per μL of erythrocyte suspension is measured by using a blood cell analyzer.

(First Erythrocyte Deformability Calculating Step (Stage 1))

A measurement apparatus mounted with a 6.00 μm nickel mesh filter as shown in FIG. 2 is used. Erythrocyte suspension is put in a glass tube with a solution sending pump, to measure the deformability. Further, the number of erythrocytes per μL of non-aged erythrocytes suspension that have passed through the 6.00 μm nickel mesh filter is measured by using a blood cell analyzer.

(Second Erythrocyte Deformability Calculating Step (Stage 2))

The non-aged erythrocyte suspension is diluted with a buffer to prepare a non-aged erythrocyte suspension. After washing inside of the measurement apparatus with a buffer, the 6.00 μm nickel mesh filter is changed to a 5.31 μm nickel mesh filter. Non-aged erythrocyte suspension is put in a glass tube with a solution sending pump, to measure the deformability. Further, the number of erythrocytes per μL of juvenile erythrocyte suspension that have passed through the 5.31 μm nickel mesh filter is measured by using a blood cell analyzer.

(Assessment Step)

By using each obtained deformability, each number of erythrocytes, the aging of blood is assessed.

Example 1

An example of using actual blood collected from human, and assessing aging of blood by following the above-mentioned basic operations is shown in the following.

By a method shown in the above-mentioned erythrocyte suspension-preparing step, an erythrocyte suspension (sample liquid) of HCT 3% was prepared from blood collected from human. The number of erythrocytes of the sample liquid at that time was $32 \times 10^4/\mu l$.

Further, for comparison, a comparative sample liquid added with 500 mM of a free radical producing substance AAPH (2,2'-azobis-2-methyl-propanimidamide, dihydrochloride) that decreases erythrocyte deformability was prepared (number of erythrocytes: $32 \times 10^4/\mu l$).

By using a 6.00 μm nickel mesh filter, and employing the technique of the above-mentioned first erythrocyte deformability calculating step (stage 1), the deformability and the number of erythrocytes were measured. As it is shown in FIG. 4 (each graph on the left), the deformability of the sample liquid and that of the comparative sample liquid in stage 1 were 93% and 90%, respectively. Further, as shown in FIG. 6 (each graph on the left), the number of erythrocytes of the sample liquid that have passed through the filter in stage 1 was $26 \times 10^4/\mu l$ (passing rate: 81%), and the number of erythrocytes of the comparative sample that have passed through the filter was $26 \times 10^4/\mu l$ (passing rate: 81%).

The deformability of erythrocytes (%) was obtained as follows. The erythrocyte suspension (sample liquid or comparative sample liquid) was allowed to pass through the nickel mesh filter from a height of 15 cm, the pressure change during passing was continuously detected, to obtain height-time curve, and the erythrocyte deformability was assessed by using the height-time curve of the buffer not containing erythrocytes as control. The deformability at the time point where it has been decreased to 10 cm was quantified by comparing with the control.

The number of erythrocytes of the sample liquid and comparative sample liquid after the first erythrocyte deformability calculating step (stage 1) was diluted and adjusted to $9 \times 10^4/\mu l$. Further, by using a 5.31 μm nickel mesh filter, and employing the technique in the above-mentioned second erythrocyte deformability calculating step (stage 2), the deformability and the number of erythrocytes were measured.

As shown in FIG. 4 (each graph on the right), the deformability of the sample liquid and that of the comparative sample in stage 2 were 95% and 66%, respectively, resulting in a big difference of about 30%. Further, as shown in FIG. 6 (each graph on the right), the number of erythrocytes of the sample liquid that have passed through the filter in stage 2 was $8 \times 10^4/\mu l$ (passing rate: 89%), and the number of erythrocytes of the comparative sample that have passed through the filter was $7 \times 10^4/\mu l$ (passing rate: 78%). The difference here was also as large as about 11%.

On the other hand, as shown in FIG. 5, by a conventional method of a single stage using only a 5.31 μm nickel mesh filter (number of erythrocytes in the sample liquid: $34 \times 10^4/\mu l$), the deformability of the sample liquid and that of the comparative sample were 89% and 80%, respectively, of which difference was as small as less than 10%. Further, as shown in FIG. 7, the erythrocytes in the sample liquid that have passed through the filter was $25 \times 10^4/\mu l$ (passing rate: 74%), and the erythrocytes of the comparative sample that have passed through the filter was $26 \times 10^4/\mu l$ (passing rate: 76%), and there was almost no difference (the comparative sample liquid showed a larger value).

As it is stated in the above, according to the method of multistage of the present invention, the state of erythrocytes can be understood with excellent accuracy, allowing an accurate assessment, as well as a more sharp classification of right and wrong.

INDUSTRIAL APPLICABILITY

The method of assessing aging of erythrocytes of the present invention can assess the aging of erythrocytes and is industrially useful.

EXPLANATION OF CODES 1. glass tube
2. nickel mesh filter
3. constant temperature water tank

The invention claimed is:

1. A method for assessing aging of erythrocytes by using at least two types of filters having a plurality of micropores, the method comprising:

preparing an erythrocyte suspension from a blood sample;

allowing the erythrocyte suspension to pass through a first filter having a diameter of micropores of 5.50 to 8.00 µm, separating aged erythrocytes that do not pass through the first filter and non-aged erythrocytes that pass through the first filter, to calculate a first deformability which is an index showing the ability of erythrocytes contained in the erythrocyte suspension to pass through the first filter;

allowing the separated non-aged erythrocyte suspension having passed through the first filter to pass through a second filter having micropores of which diameter is 3.00 to 6.00 µm, and smaller than the diameter of micropores of the first filter, separating mild aged erythrocytes that do not pass through the second filter and juvenile erythrocytes that pass through the second filter, to calculate a second deformability which is an index showing the ability of the non-aged erythrocytes contained in the non-aged erythrocyte suspension to pass through the second filter; and assessing aging of erythrocytes based on a size of the first deformability of erythrocytes contained in the erythrocyte suspension, and the second deformability of the non-aged erythrocytes.

2. The method for assessing aging of erythrocytes according to claim 1, wherein a passing ratio of erythrocytes of the first filter and/or a passing ratio of erythrocytes of the second filter is further calculated, to use the passing ratio for the assessment.

* * * * *